(12) United States Patent
Yu et al.

(10) Patent No.: US 7,468,605 B2
(45) Date of Patent: Dec. 23, 2008

(54) **SIMULTANEOUS CHEMICAL SPECIES SEPARATION AND $T_2^*$ MEASUREMENT USING MRI**

(75) Inventors: Huanzhou Yu, Mountain View, CA (US); Scott B. Reeder, Middleton, WI (US); Charles A. McKenzie, London (CA); Angel R. Pineda, Fullerton, CA (US)

(73) Assignee: The Board of Trustees of the Leland Stanford Junior University, Palo Alto, CA (US)

( * ) Notice: Subject to any disclaimer, the term of this patent is extended or adjusted under 35 U.S.C. 154(b) by 0 days.

(21) Appl. No.: 11/738,350

(22) Filed: Apr. 20, 2007

(65) Prior Publication Data
US 2007/0247153 A1    Oct. 25, 2007

Related U.S. Application Data

(60) Provisional application No. 60/745,602, filed on Apr. 25, 2006.

(51) Int. Cl.
*G01V 3/00* (2006.01)

(52) U.S. Cl. ................................. 324/309; 324/307

(58) Field of Classification Search ........... 324/309, 324/307, 306
See application file for complete search history.

(56) References Cited

U.S. PATENT DOCUMENTS

| | | | |
|---|---|---|---|
| 5,910,728 A | 6/1999 | Sodickson | |
| 6,289,232 B1 | 9/2001 | Jakob et al. | |
| 6,377,045 B1 | 4/2002 | Van Den Brink et al. | |
| 6,605,943 B1 * | 8/2003 | Clark et al. | 324/309 |
| 6,714,010 B2 | 3/2004 | Madore | |
| 6,836,114 B2 * | 12/2004 | Reddy et al. | 324/307 |
| 7,298,144 B2 | 11/2007 | Reeder et al. | |
| 7,349,729 B2 | 3/2008 | Reeder et al. | |

OTHER PUBLICATIONS

An et al., "Chemical Shift Imaging with Spectrum Modeling", Magn. Reson. Med. (2001) 46(1):126-130.

An et al., "Water-Fat Imaging with Three Orthogonal-Phase Acquisitions", Proceedings 6th Scientific Meeting, International Society for Magnetic Resonance in Medicine (1998), 1866.

Brau et al., "Accelerated IDEAL Water-Fat Separation Techniques for Single- and Multi-Coil Applications", Proc. Int. Soc. Mag. Reson. Med. 13 (2005) p. 491.

Bydder et al., "Fat Quantification by Modeling the Variation in Signal Amplitude with TE", Proc. Int. Soc. Mag. Reson. Med. 14 (2006) p. 2298.

Dixon, "Simple Proton Spectroscopic Imaging", Radiology (1984) 153:189-194.

(Continued)

*Primary Examiner*—Louis M Arana
(74) *Attorney, Agent, or Firm*—Beyer Law Group LLP

(57) ABSTRACT

A method for generating a magnetic resonance image is provided. A magnetic resonance imaging excitation is applied for a plurality of cycles at a cycle rate. A plurality of magnetic resonance image echoes is acquired for each cycle. A decay map is estimated from the plurality of magnetic resonance image echoes for each cycle. The estimated decay map is used to generate an image for at least two different species.

20 Claims, 9 Drawing Sheets

OTHER PUBLICATIONS

Fernandez-Real et al., "Cross-Talk between Iron Metabolism and Diabetes", Diabetes (2002), 51(8):2348-2354.

George et al., "Increased Hepatic Iron Concentration in Nonalcoholic Steatohepatitis is Associated with Increased Fibrosis", Gastroenterology (1998), 114(2):311-318.

Glover, G., "Multipoint Dixon Technique for Water and Fat Proton and Susceptibility Imaging", Journal of Magnetic Resonance Imaging (1991), 1:521-530.

McKenzie et al., "Abdominal Three Point Dixon Imaging with Self Calibrating Parallel MRI", in Proc. Intl. Soc. Mag. Reson. Med. 11 (2004), p. 917.

Moirand et al., "A New Syndrome of Liver Iron Overload with Normal Transferin Saturation", The Lancet (1997); 349 (9045):95-97.

Pineda et al., "Cramer-Rao Bounds for Three-Point Decomposition of Water and Fat", Magn. Reson. Med. (2005) 54(3):625-635.

Reeder et al., "Iterative Decomposition of Water and Fat with Echo Asymmetry and Least-Squares Estimation (IDEAL): Application with Fast Spin-Echo Imaging", Magn. Reson. Med. (2005), 54(3):636-644.

Reeder et al., "Multicoil Dixon Chemical Species Separation with an Iterative Least-Squares Estimation Method", Magn. Reson. Med. (2004) 51:35-45.

Westphalen et al., "Liver Fat: Effect of Hepatic Iron Deposition on Evaluation with Opposed-Phase MR Imaging", Radiology (2007), 242(2):450-455.

Wieben et al., "Multi-Echo Balanced SSFP IMaging for Iterative Dixon Reconstruction", Proc. Intl. Soc. Mag. Reson. Med. 13 (2005), p. 2386.

Yu et al., "Field Map Estimation with a Region Growing Scheme for Iterative 3-Point Water-Fat Decomposition", Magn. Reson. Med. (2005) 54(3):1032-1039.

Yu et al., "Single Acquisition Water-Fat Separation: Feasibility Study for Dynamic Imaging", Magn. Reson. Med. (2006) 55(2): 413-422.

Yu et al., "Single Quadrature Echo Water-Fat Separation with Robust Phase Correction", Proc. Intl. Soc. Mag. Reson. Med. 14 (2006), p. 2446.

U.S. Appl. No. 10/690,230, by Reeder et al. entitled "Magnetic Resonance Imaging of Different Chemical Species in a System Having Magnetic Field Heterogeneitirs", filed on Oct. 23, 2003 (published).

Office Action dated Jun. 18, 2008 from U.S. Appl. No. 11/738,345.

\* cited by examiner

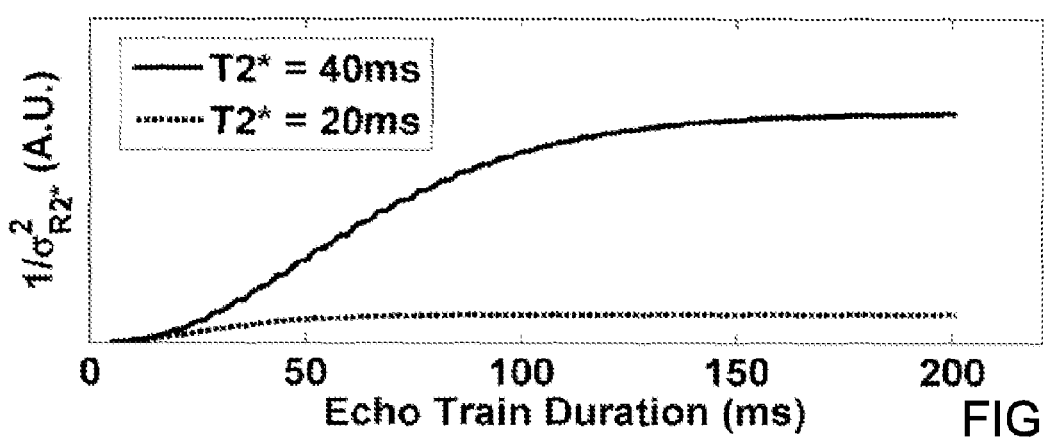
FIG. 2A
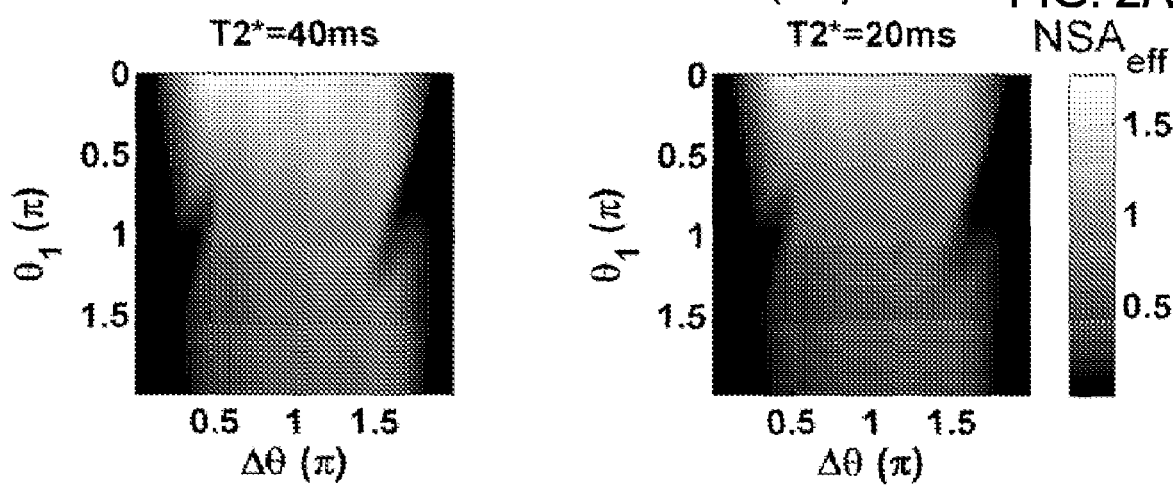
FIG. 2B
FIG. 2C
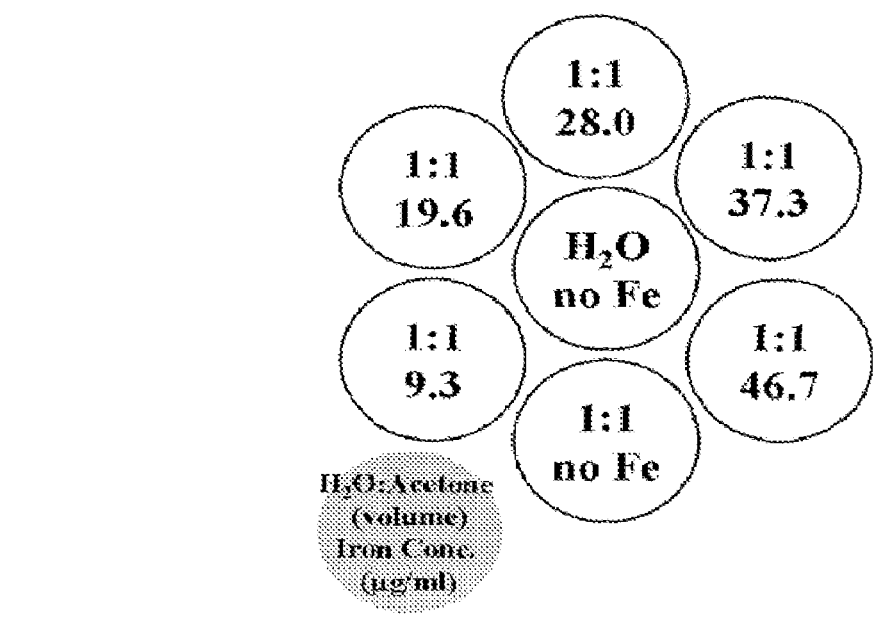
FIG. 3

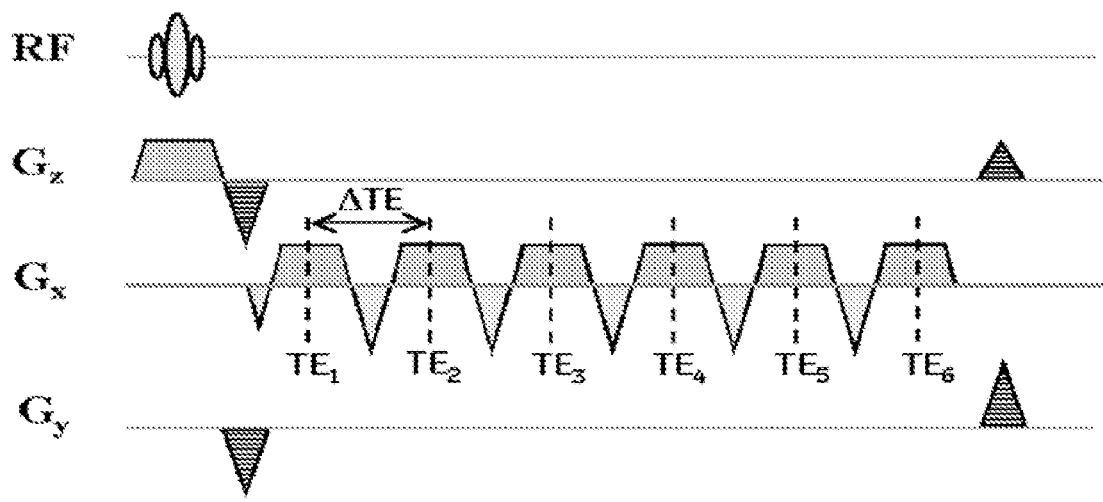
FIG. 4
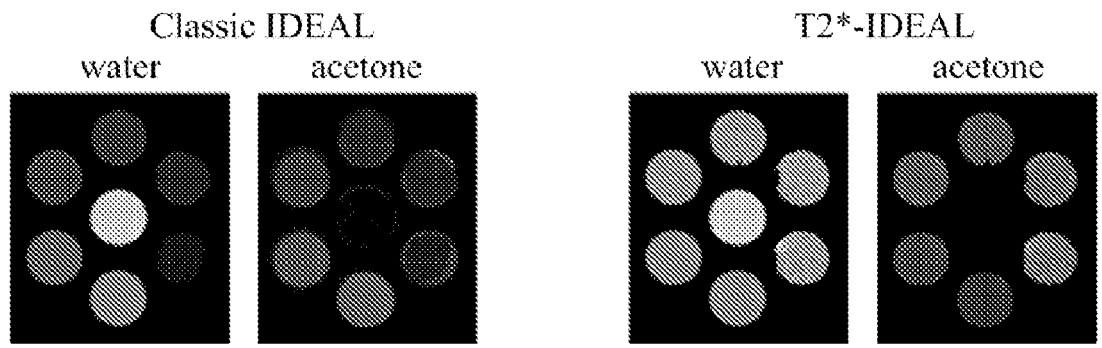
FIG. 5A  FIG. 5B  FIG. 5C  FIG. 5D
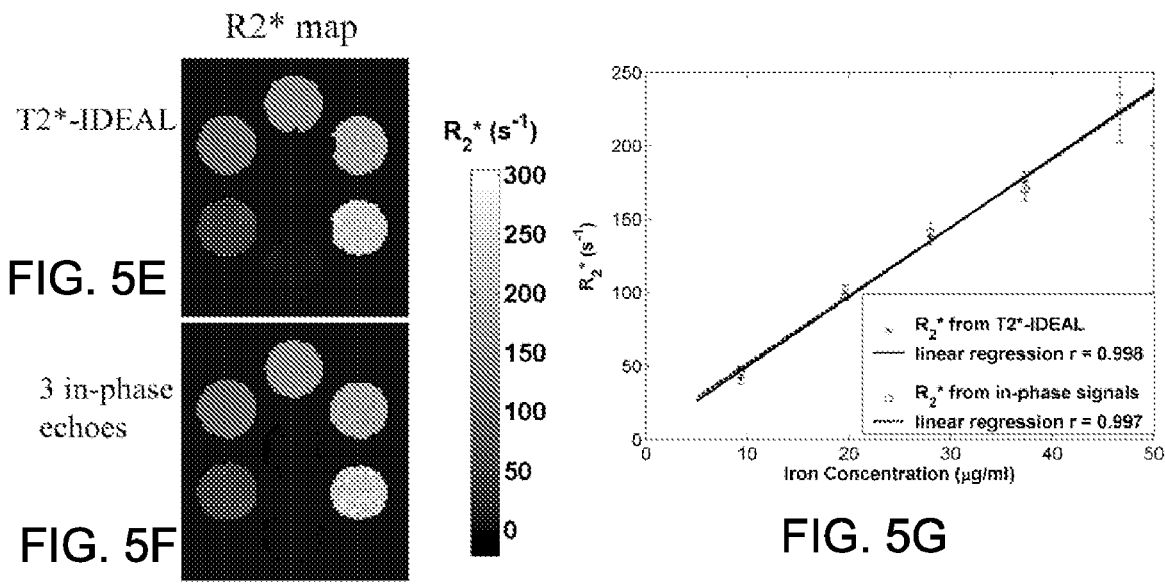
FIG. 5E
FIG. 5F
FIG. 5G

FIG. 8A
FIG. 8B
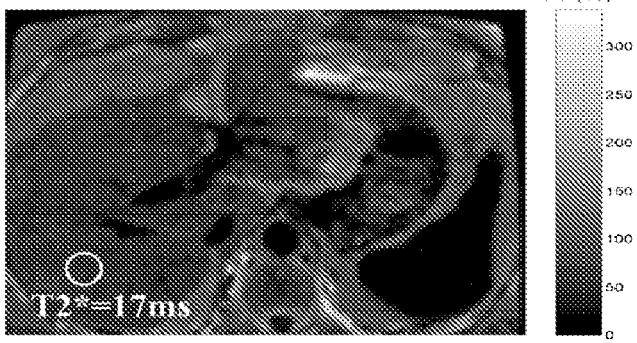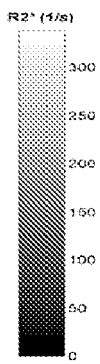
FIG. 8C
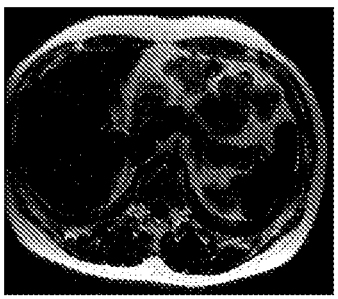
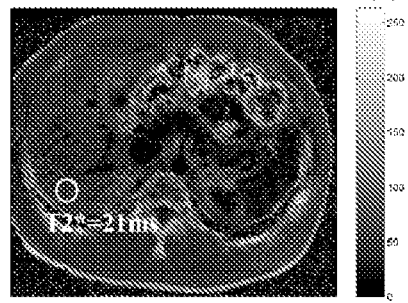
FIG. 9A
FIG. 9B
FIG. 9C
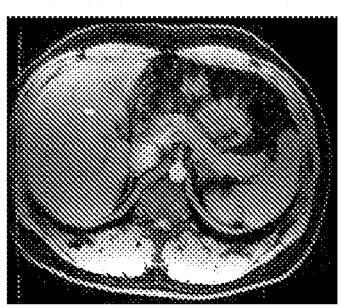
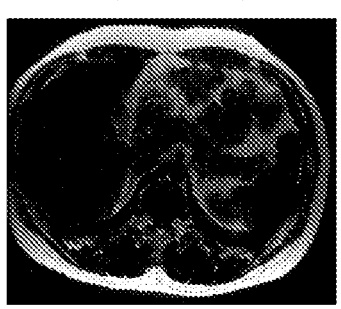
FIG. 9D
FIG. 9E

SIMULTANEOUS CHEMICAL SPECIES SEPARATION AND $T_2^*$ MEASUREMENT USING MRI

CROSS REFERENCE TO RELATED APPLICATIONS

This application claims priority under 35 U.S.C. §119 from U.S. Provisional Patent Application No. 60/745,602, filed Apr. 25, 2006, entitled MRI METHODS FOR COMBINING SEPARATE SPECIES AND QUANTIFYING A SPECIES, which is incorporated herein by reference for all purposes.

GOVERNMENT RIGHTS

The U.S. government has rights in the disclosed invention pursuant to NIH Grant No. P41RR09784 to Stanford University.

BACKGROUND OF THE INVENTION

This invention relates generally to magnetic resonance imaging of an object having different chemical species therein, such as fat and water, and more particularly, the invention relates to species imaging in the presence of magnetic field heterogeneity and transverse magnetization relaxation ($T2^*$ decay).

Reliable and uniform fat suppression is essential for accurate diagnoses in many areas of MRI. This is particularly true for sequences such as fast spin-echo (FSE), steady-state free precession (SSFP) and gradient echo (GRE) imaging, in which fat is bright and may obscure underline pathology. Although conventional fat saturation may be adequate for areas of the body with relative homogeneous $B_0$ field, there may be many applications in which fat saturation routinely fails. This is particularly true for extremity imaging, off-isocenter imaging, large field of view (FOV) imaging, and challenging areas such as the brachial plexus and skull based, as well as many others. Short-TI inversion recovery (STIR) imaging provides uniform fat suppression, but at a cost of reduced signal-to-noise ratio (SNR) and mixed contrast that is dependent on $T_1$. This latter disadvantage limits STIR imaging to $T_2$ weighted ($T_2W$) applications, such that current $T_1$, weighted ($T_1W$) applications rely solely on conventional fat-saturation methods. Another fat suppression technique is the use of spectral-spatial or water selective pulses; however, this method is also sensitive to field inhomogeneities.

"In and Out of Phase" imaging was first described by Dixon in "Simple Proton Spectroscopic Imaging," Radiology (1984) 153:189-194, and was used to exploit the difference in chemical shifts between water and fat in order to separate water and fat into separate images. Glover et al. further refined this approach, described in Glover G., "Multipoint Dixon Technique for Water and Fat Proton and Susceptibility Imaging," Journal of Magnetic Resonance Imaging (1991) 1:521-530, with a 3-point method that accounts for magnetic field inhomogeneities created by susceptibility differences. This method was applied with FSE imaging by acquiring three images with the readout centered at the spin-echo for one image and symmetrically before and after the spin-echo in the subsequent two images.

SUMMARY OF THE INVENTION

To achieve the foregoing and in accordance with the purpose of the present invention, a method for generating a magnetic resonance image is provided. A magnetic resonance imaging excitation is applied for a plurality of cycles at a cycle rate. A plurality of magnetic resonance image echoes is acquired for each cycle. A transverse magnetization decay map is estimated from the plurality of magnetic resonance image echoes for each cycle. The estimated decay map is used to generate an image for at least two different species.

In another manifestation of the invention, an apparatus for providing magnetic resonance images is provided. A magnet system is provided. A controller is electrically connected to the magnet system. The controller comprises a display, at least one processor, and computer readable media. The computer readable media comprises computer readable code for applying a cyclical magnetic resonance imaging excitation for a plurality of cycles at a cycle rate, computer readable code for acquiring a plurality of magnetic resonance image echoes for each cycle, computer readable code for estimating a decay map from the plurality of magnetic resonance image echoes for each cycle, computer readable code for using the estimated decay map to generate an image for at least two different species, and computer readable code for displaying the generated image on the display.

The invention, objects, and features thereof will be more readily apparent from the following detailed description and appended claims when taken with the drawings.

BRIEF DESCRIPTION OF THE DRAWINGS

FIG.'s 1A and B are graphs of $T2^*$ measured from signals acquired at multiple time points, which are then fit to an exponential decay.

FIG.'s 2A-C are illustrations of noise performance results.

FIG. 3 illustrates the composition of phantom tubes used in phantom experiments.

FIG. 4 is a sequence diagram.

FIG.'s 5A-G show the decomposed water and acetone images from the 3-pt phantom experiments.

FIG.'s 6A-C show a separate experiment performed on two water-only phantom tubes, one of which is also doped with SPIO particles.

FIG.'s 7A-F show images from a patient with known genetic hemochromatosis and the resulting severe hepatic iron overload.

FIG.'s 8A-C show results from a patient with mild iron deposition.

FIG.'s 9A-E show results of vivo scans performed on a healthy volunteer.

FIG.'s 10A-E show results from a patient with known hepatic steatosis.

Figure 11:
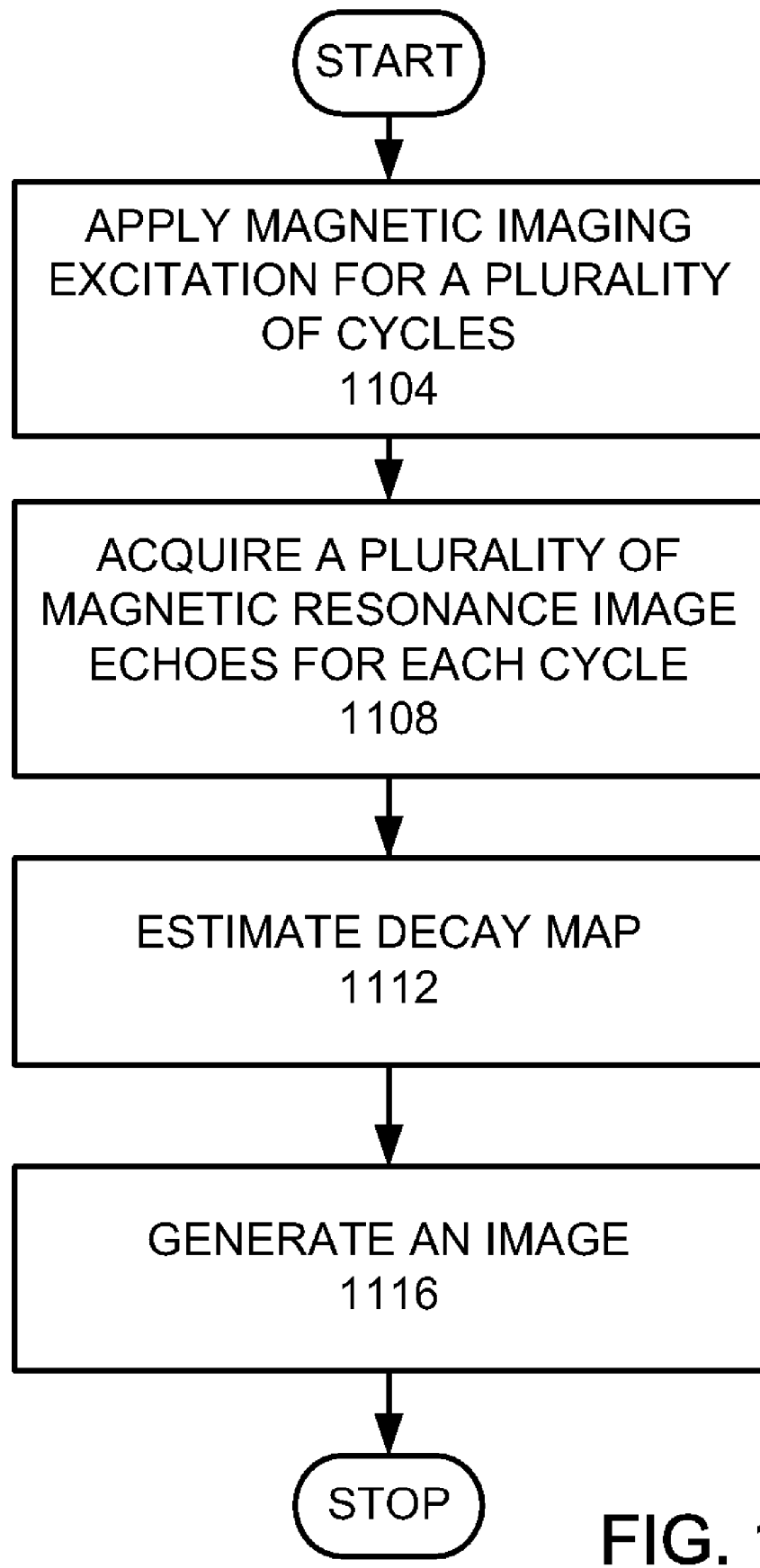

FIG. 11 is a flow chart of an embodiment of the invention.

Figure 12:
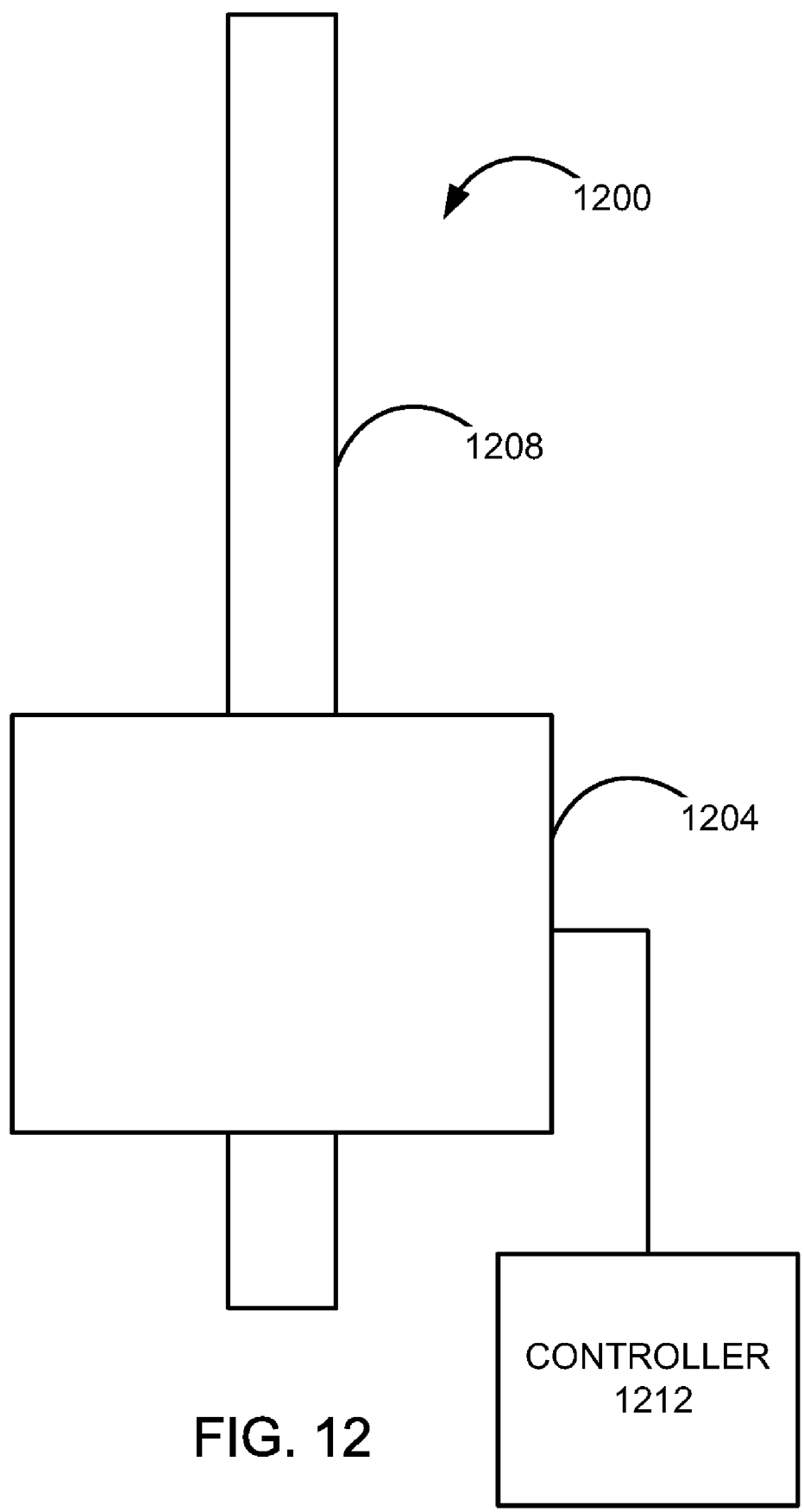

FIG. 12 is a schematic top view of a magnetic resonance imaging (MRI) system 200 that may be used in an embodiment of the invention.

FIG.'s 13A and 13B illustrate a computer system, which is suitable for implementing a controller 212 used in embodiments of the present invention.

DETAILED DESCRIPTION OF ILLUSTRATED EMBODIMENTS

In performing species decomposition, it has been found that the presence of a shortened $T2^*$ decay causes an interference, which make such processes less accurate. For example, an increasing concentration of iron (Fe) will increase inaccuracies in measuring fat and water concentration. On the other hand, measurements of the concentration of iron would be made inaccurate if water and fat co-exist.

MRI is increasingly important for the characterization of diffuse liver diseases. Non-Alcoholic Fatty Liver Disease (NAFLD) is now recognized as one of the most common chronic liver disease, affecting up to 20% of the United States population. Hepatic steatosis, or fatty infiltration of the liver, is the primary feature and the earliest manifestation of NAFLD. MRI is emerging as a valuable non-invasive tool for early detection and monitoring of steatosis. Hepatic iron overload resulting from diseases, including genetic hemochromatosis and transfusional hermosiderosis, is also a common chronic liver disease, which may eventually lead to cirrhosis, liver failure and development of hepatocellular carcinoma. The excessive concentration of iron in the liver tissue produces significant signal dephasing and $T2^*$ shortening, reducing $T2^*$ in liver to as short as 2 or 3 ms in extreme cases. MRI has been shown to have excellent sensitivity to the presence of iron with $T2^*$ weighted sequences. It has been demonstrated that $R2^*$ ($=1/T2^*$) is strongly correlated with liver iron and the relationships between MRI measured $R2^*$ and biopsy obtained HIC have been derived in various studies. Furthermore, the co-occurrence of hepatic steatosis and iron overload is increasingly recognized as being very common. Although the exact interaction between the two conditions remains unclear, George DK, Goldwurm S, MacDonald GA, Cowley LL, Walker NI, Ward PJ, Jazwinska EC, Powell LW. Increased hepatic iron concentration in nonalcoholic steatohepatitis is associated with increased fibrosis. Gastroenterology 1998; 114(2):311-318 found 31% of patients with steatosis have the HFE hemochromatosis mutation. Moirand R, Mortaji AM, Loreal O, Paillard F, Brissot P, Deugnier Y. A new syndrome of liver iron overload with normal transferring saturation and Lancet 1997;349(9045):95-97. Fernandez-Real JM, Lopez-Bernejo A, Ricart W. Cross-talk between iron metabolism and diabetes. Diabetes 2002;51(8):2348-2354 presented evident associations between iron accumulation and diabetes, one of the risk factors for steatosis. It is, therefore, very important to consider the possible presence of iron when attempting to quantify steatosis and vice versa.

Conventional methods of measuring liver fat content or iron deposition using MRI both rely on signal intensity changes among multiple echoes. The amount of fat in liver can be determined from water and fat images decomposed from multi-point chemical shift based techniques, known as the 2-point (2-pt) and 3-point (3-pt) "Dixon" methods. However, it has been assumed that $T2^*$ decay results in negligible signal loss among the echoes, which is valid for most applications. In the presence of iron deposition, however, $T2^*$ shortening may be significant on the time scale of Dixon echo shifts, severely compromising the estimation of fat. It has been shown that a rapid $T2^*$ decay may lead to substantial errors in hepatic fat estimates, and a $T2^*$ map must be collected separately for correction. Bydder M, Middleton M, Sirlin C, Gatehouse P, Chavez A. "Fat Quantification by Modeling the Variation in Signal Amplitude with TE," 2006 May; Seattle. p 2298 showed that the 2-pt Dixon can underestimate the fat-signal fraction when the $T2^*$ is short. Westphalen AC, Qayyum A, Yeh BM, Merriman RB, Lee JA, Lamba A, Lu Y, Coakley FV. "Liver Fat: Effect of Hepatic Iron Deposition on Evaluation With Opposed-Phase MR Imaging," Radiology 2007;242(2):450-455 reported that no correlation was found between the radiologist reading and biopsy when quantifying liver fat for iron deposition patients. There have been brief attempts to correct for or estimate $T2'/T2^*$ decay for 3-pt FSE Dixon methods. One approach normalizes the signal intensity to a 3-echo averaged value as a simple $T2^*$ compensation, as described in An L, Xiang Q-S "Water-Fat Imaging with Three Orthogonal-Phase Acquisition," Proceedings 6th Scientific Meeting, International Society for Magnetic Resonance in Medicine 1998:1866, however, it requires the signals acquired at $[\pi/2, \pi/2, 3\pi/2]$ and no $T2'/T2^*$ mapping has been shown. Glover GH "Multipoint Dixon Technique for Water and Fat Proton and Susceptibility Imaging," J Magn Reson Imaging 1991;1(5):521-530. uses two in-phase echoes (0 and $2\pi$) out of the three acquired echoes to calculate the $T2'$ value. Again, the method is only valid for specific echo times and the signals from only two echoes contribute to the $T2'$ estimation therefore it is less SNR efficient, which will further reduce the SNR of the water and fat images. A promising technique that models the effects from both fat and $T2^*$ is described by Bydder et al, where the multi-echo magnitude images are used to estimate $T2^*$ and signal intensity of water and fat. However, it is challenging to distinguish water and fat without further assumption and its clinical feasibility is yet to be seen.

Figure 1A:
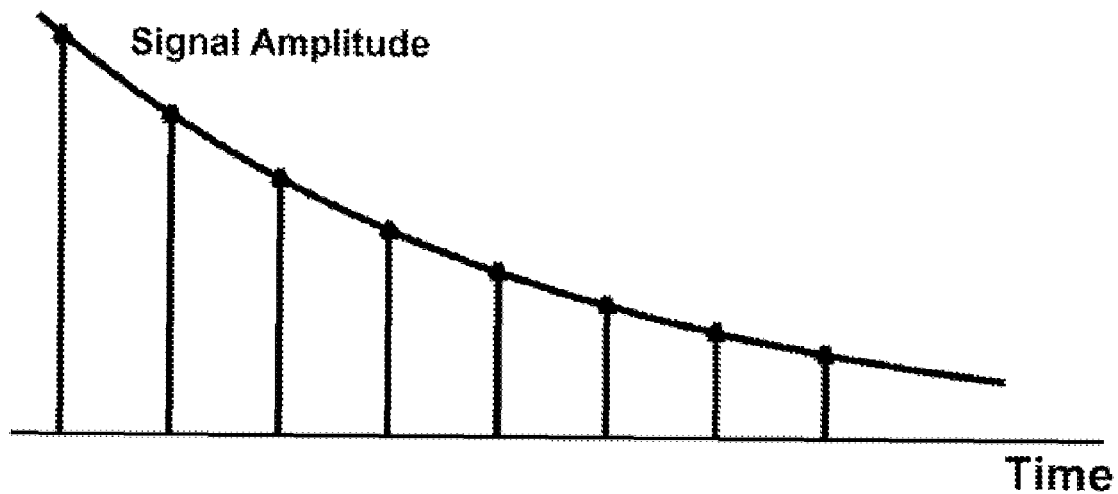
Figure 1B:
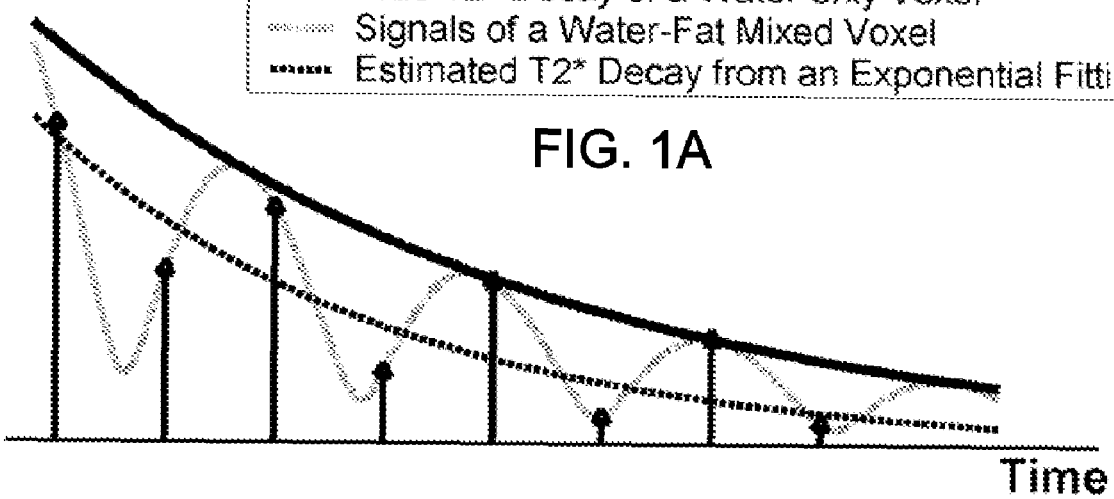

Likewise, any method that attempts to measure $T2^*$ may be confounded by the possible presence of steatosis. Liver to muscle (L/M) and liver to fat (L/F) signal intensity ratios offer reliable means to characterize liver iron content, however, are incompatible with scans using phased-array coils. Direct measurement of $T2^*$ may be a more attractive approach to quantify Hepatic Iron Concentration (HIC) independent of pulse sequence parameters such as echo times. $T2^*$ relaxometry is usually achieved by single-echo-per-TR or more recently multi-echo-per-TR gradient-recalled echo (GRE) sequences, however, may be disturbed by the chemical shift of fat. FIG. 1A shows a $T2^*$ fitting without fat. $T2^*$ is typically obtained by fitting signals collected at multiple time points to an exponential decay. For a water-only voxel, the signals follow an exponential decay curve. The arrows represent the sampling times (echo times). FIG. 1B shows a $T2^*$ fitting in the presence of fat (60% water and 40% fat). The signals no longer follow an exponential decay due to constructive and destructive interference of the water and fat signals. Therefore, an erroneous $T2^*$ may be estimated if the effect of the chemical shift is not considered. This error can be avoided if signals are sampled when water and fat are in-phase (multiples of 4.8 ms at 1.5 T). However, this strategy results in a limited estimable range of $T2^*$ and long repetition times (TR), hampering its use in time-sensitive applications, such as breath-held liver imaging.

A recently developed multi-point iterative reconstruction algorithm, based on the "Dixon" method and known as IDEAL (Iterative Decomposition of water and fat with Echo Asymmetry and Least-squares estimation), allows water-fat decomposition with flexible echo sampling times and more than three echoes, as discussed in Reeder SB, Wen Z, Yu H, Pineda AR, Gold GE, Markl M, Pelc NJ. "Multicoil Dixon Chemical Species Separation With an Iterative Least-Squares Estimation Method," Magn Reson Med 2004;51(1):35-45 and Reeder SB, Pineda AR, Wen Z, Shimakawa A, Yu H, Brittain JH, Gold GE, Beaulieu CF, Pelc NJ "Iterative Decomposition of Water and Fat with Echo Asymmetry and Least-Squares Estimation (IDEAL): Application with Fast Spin-Echo Imaging," Magn Reson Med 2005;54(3):636-644. This flexibility enables optimization of the sequence parameters such that the water and fat images decomposed with IDEAL have the maximum possible SNR. In addition, IDEAL is naturally compatible with multi-coil acquisitions and parallel imaging reconstruction. Given these considerations, IDEAL has great potential for quantitative evaluation of fatty infiltration in the liver. However, like the Dixon methods, it neglects the $T2^*$ decay, therefore, $T2^*$ cannot be estimated and may interfere the fat quantification.

An embodiment of the invention provides a new reconstruction algorithm to achieve simultaneous estimation of tissue water content, fat content, and T2*. A novel construct of a "complex field map" is used to include the effects of T2*, which is assumed to be equal for water and fat. The IDEAL algorithm is then modified to estimate the "complex field map", thus achieving estimation of T2* even in the presence of fat. The technique de-couples the effects of fat-induced chemical shift and iron-induced T2* decay, thereby providing more accurate water-fat decomposition and estimation of T2*. A multi-echo GRE sequence is used that is capable of acquiring a flexible number of echoes (up to sixteen) in one TR. Results from 3-pt (3-echo) phantom experiments and 6-pt (6-echo) in-vivo abdominal scans are presented. Like the conventional IDEAL algorithm (referred to as "classic IDEAL" in this work), this embodiment of the invention (called "T2*-IDEAL") permits reconstruction from flexible echo times and number of echoes and thus data can be acquired as rapidly as possible. As a result, it is possible to achieve both water-fat decomposition and T2* estimation in a single breath-hold.

Theory:

T2*-IDEAL reconstruction with weighted least squares inversion

In the presence of iron overload, this embodiment of the invention assumes that the shortened T2* effect is dominated by the presence of iron, and as a result, the water and fat components that co-exist in the same voxel have similar values of T2*. The signals ($S_i$) of a voxel at the echo times ($t_i$, i=1, 2, 3... k, k=number of echoes acquired) can be represented as:

$$s_i = (w + f \cdot e^{j2\pi\Delta f t_i}) \cdot e^{j2\pi\psi t_i} \cdot e^{-R_2^* t_i} + n_i \quad [1]$$
$$= (w + f \cdot e^{j2\pi\Delta f t_i}) \cdot e^{j2\pi(\psi + jR_2^*/2\pi)t_i} + n_i$$
$$= (w + f \cdot e^{j2\pi\Delta f t_i}) \cdot e^{j2\pi\hat{\psi} t_i} + n_i$$

where w and f denote the water and the fat components in this voxel, respectively. $\Delta f$ is the chemical shift of fat with respect to water. $\psi$ represents the $B_0$ field inhomogeneity (in Hz), or field map, at this voxel. $n_i$ is the noise in the signal. R2* is used for convenience. Furthermore, a "complex field map" is introduced:

$$\hat{\psi} = \psi + j\frac{R_2^*}{2\pi} \quad [2]$$

With this "complex field map", $\hat{\psi}$, Equation [1] has the same form as the signal model used in the IDEAL algorithm. Therefore, water, fat and $\hat{\psi}$ can be calculated in a similar way as the classic IDEAL algorithm. First, the "complex field map" $\hat{\psi}$ is solved using the iterative algorithm described in Reeder et al., with the adjustment of treating $\hat{\psi}$ as a complex value, the details of which are described below. The converged value of $\hat{\psi}$ is then decomposed with the real and imaginary parts assigned to the field map and the R2* map estimates. The source signals are demodulated by $\hat{\psi}$, thereby correcting for both $B_0$ field inhomogeneity and T2* decay simultaneously, as denoted in Eq. [3]

$$S'_i = S_i \cdot e^{-j2\pi\hat{\psi} t_i} = W + f \cdot e^{j2\pi\Delta f t_i} + n_i \cdot e^{-j2\pi\hat{\psi} t_i} \quad [3]$$

Considering all echoes, Equation [3] can be formulated in a matrix form:

$$s' = \begin{bmatrix} s'_1 \\ s'_2 \\ \cdots \\ s'_k \end{bmatrix} = \begin{bmatrix} 1 & e^{j2\pi\Delta f t_1} \\ 1 & e^{j2\pi\Delta f t_2} \\ \cdots & \\ 1 & e^{j2\pi\Delta f t_k} \end{bmatrix} \cdot \begin{bmatrix} w \\ f \end{bmatrix} + \begin{bmatrix} n_1 e^{-j2\pi\hat{\psi} t_1} \\ n_2 e^{-j2\pi\hat{\psi} t_2} \\ \cdots \\ n_k e^{-j2\pi\hat{\psi} t_k} \end{bmatrix} \quad [4]$$

$$= A \cdot \begin{bmatrix} w \\ f \end{bmatrix} + n'$$

Note that with the T2* correction, the variance of the noise (n') is no longer equal for all echoes:

$$\text{var}(s'_i) = \text{var}(n'_i) = \text{var}(n_i) \cdot e^{2R_2^* t_i} \quad [5]$$

Equation [5] suggests that the source signals after correction for field map and T2* (s') have less noise at earlier echoes, which is an intuitive result as signals decay away exponentially. To account for the different noise variance, unlike the classic IDEAL algorithm, where a linear least squares inversion is used, this embodiment obtains water and fat components from a weighted least squares inversion, shown in the following Equation:

$$\begin{bmatrix} w \\ f \end{bmatrix} = (A^T \cdot W \cdot A)^{-1} \cdot A^T \cdot W \cdot s' \quad [6]$$

where the weights are given by $W = \text{diag}(e^{2R_2^* t_1}, e^{2R_2^* t_2}, \ldots e^{2R_2^* t_k})$. The value of R2* is obtained from the iterative estimation of $\hat{\psi}$ as described earlier.

Noise Performance

The T2*-IDEAL method essentially includes a process of fitting the signals to an exponential decay, where typically 5-20 echoes have been used in the context of R2* mapping in liver, as described in St Pierre TG, Clark PR, Chua-Anusorn W "Single Spin-Echo Proton Transverse Relaxometry of Iron-Loaded Liver," NMR Biomed 2004;17(7):446-458. Acquiring more than three echoes improves T2* estimation and correction but results in increased scan time through an increased TR. Therefore, the number of echoes should be chosen based on a tradeoff between reasonable scan time and improved T2* fitting.

The SNR performance of a water-fat decomposition method can be quantified by the Cramer-Rao bound (CRB), which is described in Pineda AR, Reeder SB, Wen Z, and Pelc NJ. Cramer-Rao "Bounds For Three-Point Decomposition of Water and Fat," Magn Reson Med 2005;54(3):625-635. The CRB predicts the minimum possible noise variance in the decomposed images that an estimator can achieve relative to the noise variance of the source images, independent of the reconstruction method. For water and fat images, the noise variance can be further translated to an upper bound of the effective NSA (Number of Signal Averages), defined in the following equation with the water image as an example:

$$NSA_{eff_w} = \frac{\sigma_s^2}{\sigma_w^2} \quad [7]$$

The CRB of the T2*-IDEAL signal model (Eq. [1]) is formulated based on the work in Pineda et al. In general, it varies with the water-fat ratio in the voxel, the echo times used, the number of echoes and the actual T2* value.

The noise performance of the R2* estimation is first studied in order to determine the number of echoes to collect. Since a multi-echo GRE sequence, described below, is used, the echo train duration is defined as $TE_1+(k-1)*\Delta TE$, i.e. the time that the last echo is acquired. Ideally, the echo train duration should be selected to minimize the noise in the estimated R2* map. FIG. 2A shows the changes of the noise variance in the R2* map with respect to the echo train duration, with a fixed noise variance in the source images and a set of $TE_1$, and $\Delta TE$ determined from a typical protocol described below. The effective NSA ($NSA_{eff}$) defined in Eq. [7] for the R2* map depends on the absolute signal intensities of water and fat; therefore, the value of $1/\sigma_{R*_2}^2$ is used and labeled with arbitrary units (A.U.). Water and fat amounts are kept constant with different echo train durations. Plots for two T2* values are presented (T2*=20 ms and T2*=40 ms). As can be seen, $1/\sigma_{R*_2}^2$ increases when more echoes are used, as expected, and becomes flat when the echo train duration is approximately 60 ms for T2*=20 ms, and 150 ms for T2*=40 ms. In other words, acquiring more echoes always helps to reduce noise in the R2* map, while the SNR increases asymptotically when the echo train duration exceeds 3-4 times the T2* value. Therefore, in order to maximize the sensitivity of the technique to a moderate iron concentration (T2* between 10 ms to 20 ms), the most efficient echo train duration needs to be no shorter than 30 ms. However, such long echo train duration significantly increases the TR and overall scan time. As a result, the breath-hold time becomes the dominant factor when determining the number of echoes.

To estimate the number of echoes that can be collected within a single breath-hold, a typical protocol is established: 256×192×36 matrix, FOV=36 cm×27 cm, 5 mm slice thickness, flip angle=15°, BW=±167 kHz and a parallel imaging reduction factor of 2. This protocol allows coverage of the entire liver for most patients, and provides in-plane resolution of 2 mm or better and 5 mm through plane resolution, sufficient to characterize a focus of steatosis. These imaging parameters lead to $TE_1$=1.1 ms and $\Delta TE$=1.8 ms at 1.5 T. Total scan time corresponding to 3-9 echoes is 16 s, 21 s, 26 s, 30 s, 35 s, 40 s and 45 s, respectively. Therefore, if a preferred breath-hold time is less than 30 seconds, no more than six echoes should be collected. With these considerations, 6-echo acquisitions are used for most of our results, which achieves a balance of short scan time and improved T2* estimation. With increasing parallel imaging accelerations or reductions in spatial resolution, longer echo trains can be used.

With a fixed number of echoes (=6), the $NSA_{eff}$ of water was studied to guide the distribution of the echo times. FIG.'s 2B and 2C show the water $NSA_{eff}$ maps predicted from the CRB. To be more general, the plots were made based on the water-fat phase shifts, defined in the following:

$\theta_i = 2\pi \cdot \Delta f \cdot t_i$, $i=1,2,\ldots k$ $\theta_1 = 2\pi \cdot \Delta f \cdot TE_1$ $$\Delta\theta = 2\pi \cdot \Delta f \cdot \Delta TE \quad [8]$$

$\theta_1$ and $\Delta\theta$ are the corresponding water-fat phase shifts of $TE_1$, and $\Delta TE$. The $NSA_{eff}$ values are calculated for all possible equally spaced six echoes with $\theta_1$ and $\Delta\theta$ ranging from 0 to $2\pi$. In general, the NSA will depend on the relative amount of water and fat in the voxel. Therefore, at each echo time combination, the minimum calculated $NSA_{eff}$ value from all water-fat ratios is shown. Water and fat $NSA_{eff}$ maps are identical, thus only the water $NSA_{eff}$ maps are presented. Plots for two representative T2* values, 40 ms (FIG. 2B) and 20 ms (FIG. 2C), are shown. The $NSA_{eff}$ values from T2*-IDEAL reconstruction is reduced from classic IDEAL due the additional degree of freedom (T2*). The correction for the T2* decay, which exponentially magnifies the relative noise in the source images, also contributes to the apparent decrease in $NSA_{eff}$. Specifically, the correction for faster T2* decay leads to more noise magnification, which explains the larger $NSA_{eff}$ values in FIG. 2B than the ones in FIG. 2C. Both $NSA_{eff}$ maps show a similar pattern of higher $NSA_{eff}$ values with a shorter $\theta_1$, which suggests that a short $TE_1$, is favored in order to improve the noise performance. With a fixed $\theta_1$, $NSA_{eff}$ is less sensitive to the change of $\Delta\theta$, unless $\Delta\theta$ is close to 0 or $2\pi$, when water and fat are close to in-phase. As a result, the minimum echo times (including minimum $TE_1$, and $\Delta TE$) can be used, provided that the corresponding $\Delta\theta$ is not close to 0 or $2\pi$. This strategy allows acquiring as many echoes as possible and achieving the best (or near best) possible noise performance without increasing the scan time.

The CRB theory predicts an upper bound of the noise performance that can be achieved by a reconstruction algorithm. Monte Carlo simulations demonstrate that the CRB bound for the water and fat estimates is achieved using the T2*-IDEAL reconstruction with the weighted least squares inversion. Therefore, T2*-IDEAL reconstruction is also an SNR efficient decomposition algorithm.

Materials and Methods:

Phantom Experiments

Phantom studies were first performed to validate the T2*-IDEAL algorithm. Acetone was used as an alternative to fat because it is soluble in water. The chemical shift of acetone was measured by spectroscopy and determined to be 2.4 ppm, or -155 Hz at 1.5 T. Equal volume of water and acetone were mixed in six 50 ml tubes, which were then doped with increasing concentrations of Feridex IV® (Berlex Laboratories, Wayne, NJ USA), a superparamagnetic iron oxide (SPIO) contrast agent that shortens T2*. The composition of the phantom tubes is illustrated in FIG. 3. The phantom consists of 7 tubes. The center tube has only water, and the rest of the tubes contain the same volume of water and acetone. They were then doped with increasing concentrations of an SPIO contrast agent that shortens T2*.

A 2D spoiled gradient echo (SPGR) IDEAL sequence was used for all phantom scans. Three echoes were acquired to simulate the most challenging situation for the T2*-IDEAL method. Echo times $t_i$=[3.8, 8.2, 12.5] ms ($\theta_i$=[5π/2−4π/3, 5π/2, 5π/2+4π/3]) were selected to achieve optimal SNR performance for classic IDEAL reconstruction. The data were processed with both the T2*-IDEAL algorithm and classic IDEAL. In addition, the phantom was imaged at three echo times chosen when water and acetone are in-phase, i.e.: $\theta_i$=[2π, 4π, 6π], $t_i$=[6.5, 13.1, 19.6] ms at 1.5 T. The in-phase echo times were chosen such that the chemical shift would not confound the R2* measurement, and R2* could be measured independently by fitting the in-phase signals to an exponential decay. Comparison between the R2* maps obtained from the two approaches was made.

In-vivo Scans

Abdominal imaging was performed to demonstrate the T2*-IDEAL technique in-vivo with 5 healthy volunteers and 12 liver patients on 1.5 T scanners (Signa HDx, GE Healthcare, Waukesha, WI). All scanning was performed after IRB (Institutional Review Board) approval and informed consent was obtained. A multi-echo 3D SPGR sequence with flyback gradients was used to acquire all necessary data in a single breath-hold. Successful classic IDEAL reconstruction has been demonstrated with multi-echo sequences. The sequence diagram is shown in FIG. 4. Up to 16 gradient echoes with equally spaced echo times were acquired in one TR.

A variety of imaging parameters were used to evaluate the flexibility of the sequence and the reconstruction technique. A minimum of 6 echoes was acquired. As described, unlike 3-pt IDEAL, it is no longer necessary to choose an echo spacing of $\Delta\theta=2\pi/3$, allowing increased flexibility in the choice of other imaging parameters, such as spatial resolution, FOV and bandwidth. In practice, the first TE ($TE_1$) ranged from 1.6 ms to 2.8 ms, and the echo spacing ($\Delta TE$) ranged from 1.6 ms to 3.2 ms. Imaging matrices ranging from 192×128 to 256×128 and slice thickness of 8 mm were used with bandwidths ranging from ±100 kHz to ±167 kHz. Scans with higher resolutions (384×256) were performed on healthy volunteers. Eight-channel cardiac and torso phased array coils were used for all volunteer and patient imaging. These imaging parameters lead to a breath-hold time between 22 and 33 seconds. An efficient autocalibrating parallel imaging technique with reduction factor of 2 was used to reduce acquisition time for high resolution scans.

All data were reconstructed with both classic IDEAL and T2*-IDEAL methods. Synthesized in-phase, out-of-phase and fat-signal fraction (fat/(water+fat)) images were created using the two methods and compared. R2* maps were also obtained from T2*-IDEAL processing. For one patient scan with fatty infiltration of liver, twelve echoes were acquired. Fat-signal fraction images were calculated from the classic IDEAL and T2*-IDEAL methods using an incremental number of echoes, starting from the first three echoes up to all 12 echoes. The purpose of this study was to illustrate the impact of T2* decay on fat quantification with the two methods.

Results:

Phantom Experiments

FIG.'s 5A-G show the decomposed water and acetone images from the 3-pt phantom experiments. Results from both classic IDEAL and T2*-IDEAL are shown. At higher SPIO concentrations with shorter T2*, the signal decay was propagated into the decomposed water (FIG. 5A) and acetone (FIG. 5B) images for classic IDEAL. In contrast, T2*-IDEAL (FIG. 5C and FIG. 5D) compensates for the signal loss from the T2* decay. The shorter T2* phantom tubes have higher signal intensity in the water and acetone images due to the known T1 shortening effect of SPIOs. Furthermore, the T2*-IDEAL method provided accurate estimates of the R2* values (FIG. 5E), demonstrating close agreement with the in-phase R2* measurements (FIG. 5F). FIG. 5G plots R2* calculated from the T2*-IDEAL method and the in-phase signals against the iron concentration. Mean values in each tube were used and error bars indicate standard deviation. A linear relation is evident, in close agreement with previous measurements of R2*. Close agreement between the two approaches suggests high confidence in the R2* estimated using the T2*-IDEAL method even with only three echoes.

Unlike the in-phase approach to measuring R2*, the T2*-IDEAL method also allows a shorter TR and separation of water and acetone signals. Therefore the invention allows the use of a plurality of magnetic resonance image echoes for each cycle where the species phase angle difference can be arbitrary. In particular, the phase difference is not limited at $k*\pi$, where k is an integer, unlike the previous approaches mentioned above (Xiang et al, and Glover et al).

Figures 6A, 6B, 6C:
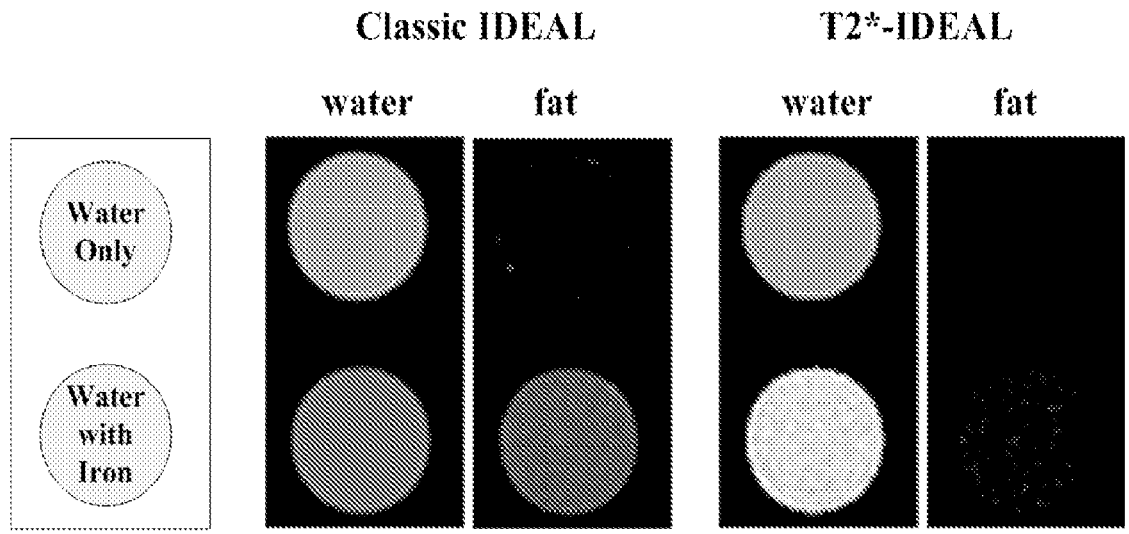

FIG.'s 6A-C show a separate experiment performed on two water-only phantom tubes, one of which is also doped with SPIO particles (T2*~10 ms). The top tube is filled with water only and the bottom tube contains water doped with the SPIO to shorten T2*. For the phantom tube with shortened T2*, approximately 19% of the signal intensity was misidentified as fat when reconstructed by the classic IDEAL method due to the confounding effects of the rapid T2* decay, as shown in FIG. 6B. In contrast, the T2*-IDEAL method models the signal intensity changes among the echoes as a T2* decay, and as a result, the phantom was correctly identified as water-only, as shown in FIG. 6C. The increased noise can be seen in the T2*-IDEAL decomposed images and is more apparent in the shortened T2* phantom tube.

In-vivo Results

Figures 7A, 7B:
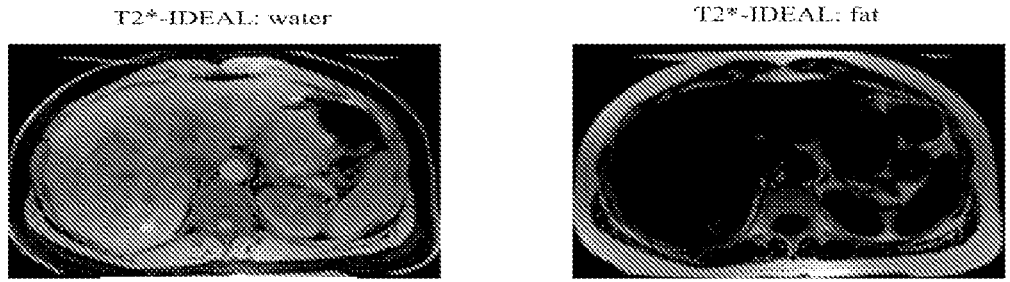
Figures 7C, 7D:
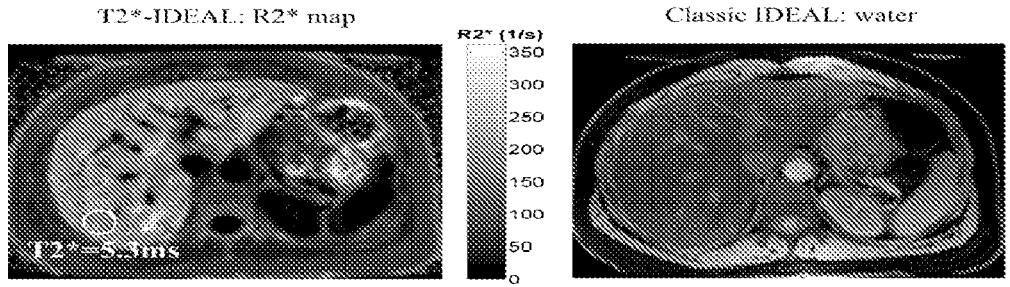
Figures 7E, 7F:
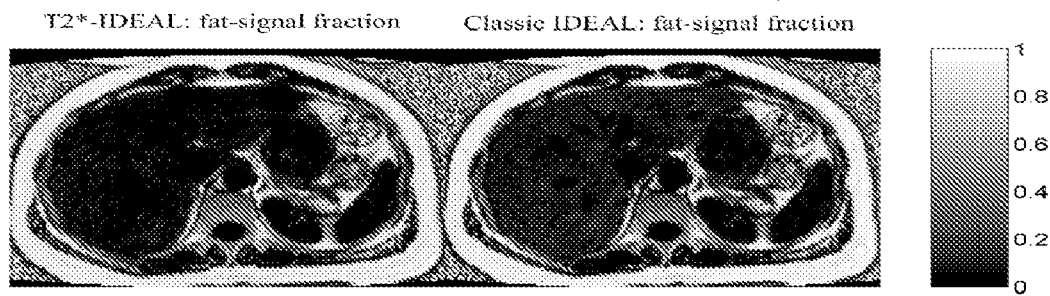

FIG.'s 7A-F show images from a patient with known genetic hemochromatosis and the resulting severe hepatic iron overload. In this acquisition, six echoes ranging from 2.0 ms to 10.8 ms were used in this acquisition. $\Delta TE=1.8$ ms. Other imaging parameters include: 224×128 matrix, FOV=35×21, BW=±143 kHz. 28 locations were covered in two 22-second breath-holds with no parallel imaging acceleration. The R2* map (FIG. 7C) demonstrates a markedly elevated R2* (shortened T2*) in the liver. The mean R2* value measured in the indicated ROI is 187 $s^{-1}$, translating to T2*=5.3 ms. Note that R2* in the spleen appears normal, typical for hemochromatosis patients where iron overload primarily affects the liver and pancreas. The T2*-IDEAL also maintains a uniform water-fat decomposition (FIG.'s 7A and B). However, the T2*-IDEAL water and fat images appear noisy due to the intrinsic low SNR of the source images with a significantly shortened T2*. As expected, the water image from classic IDEAL shows low signal intensity (FIG. 7D). In addition, due to the interference from the T2* decay, classic IDEAL reconstruction results in a biased, 11% fat-signal fraction (FIG. 7F) in liver. This bias is not present from T2*-IDEAL reconstruction, consistent with biopsy findings for this patient, which showed no steatosis (FIG. 7E).

Results from a patient with mild iron deposition are presented in FIG.'s 8A-C. The mean R2* value measured in the indicated ROI is 60 $s^{-1}$ (FIG. 8C), corresponding to T2*=17 ms, suggesting the presence of mild iron. Like the results in FIG.'s 7A-F, no shortened T2* decay is seen in the spleen. The decomposed water and fat images (FIG.'s 8 A and B) show only a moderate noise magnification with the correction for a mild T2* decay. Six echoes were collected, $TE_1=2.0$ ms, $\Delta TE$ 1.6 ms. Other imaging parameters include: 192×28 matrix, 35×28 cm FOV, BW=±125 kHz. 24 locations were covered in a 29-second breath-hold without the use of parallel imaging.

In-vivo scans were also performed on 5 healthy volunteers and a representative case is shown in FIG.'s 9A-E. A higher imaging matrix (384×256) was used for these scans. As a result, the minimum possible echo spacing was extended to 2.7 ms ($\Delta\theta=1.1\pi$). The strategy of using this minimum echo spacing in combination with a parallel imaging reduction factor of 2, ensures a total scan time (33 seconds) achievable with a single breath-hold for normal volunteers. Six echoes were collected, $TE_1=1.6$ ms. Other imaging parameters include: 33×2 6 cm FOV, BW=±167 kHz. 10 locations. The $T2^*$ values measured from the $R2^*$ map are 21 ms in liver, consistent with typical $T2^*$ values of healthy volunteers reported in other studies. FIG.'s 9A-C are water, fat and $R2^*$ images from $T2^*$-IDEAL reconstruction, respectively. FIG.'s 9D-E are water and fat images from classic IDEAL reconstruction.

Figures 10A, 10B, 10C:
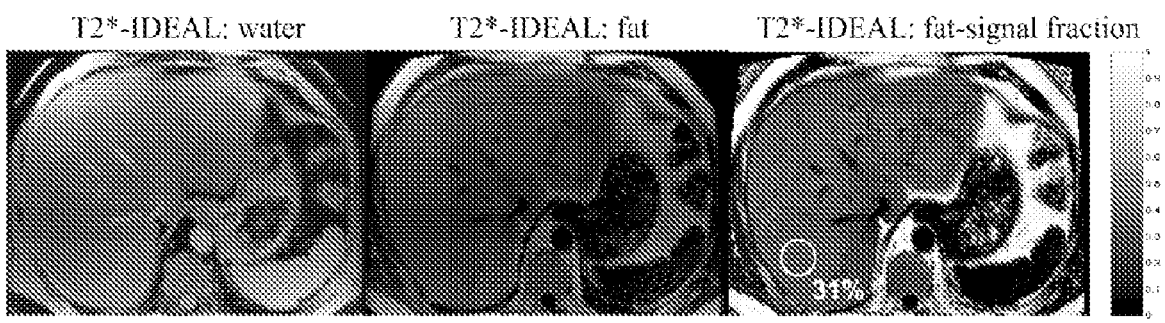
Figure 10D:
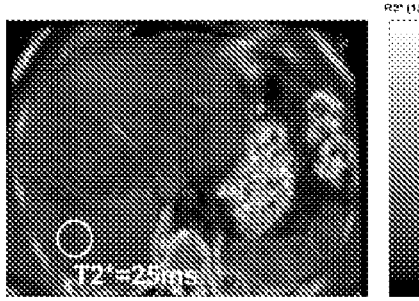
Figure 10E:
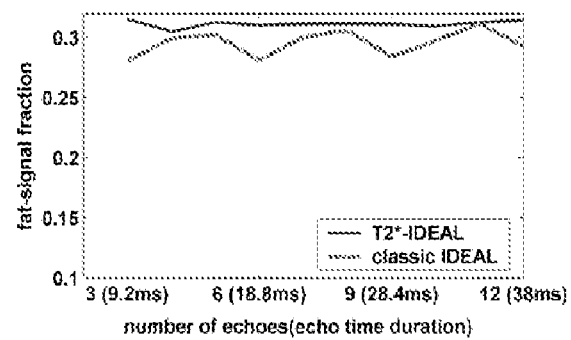

Finally, results from a patient with known hepatic steatosis are shown in FIG.'s 10A-E. Twelve echoes were collected for this acquisition, although the images FIG.'s 10A-D shown are from $T2^*$-IDEAL reconstruction using the first 6 echoes. The decomposed water and fat images (FIG. 10A, B) clearly show an abnormal amount of fat content in liver. The fat-signal fraction image (FIG. 10C) confirms this observation, with measured mean fat-signal fraction of 31% in the ROI. The $R2^*$ map suggested no shortened $T2^*$ in liver ($T2^*$~25 ms) for this patient. Furthermore, images were reconstructed using both classic IDEAL and $T2^*$-IDEAL with an increasing number of echoes, starting from the first three echoes up to all 12 echoes. The corresponding fat-signal fraction images were obtained. Mean fat-signal fraction values in the ROI (FIG. 10E) are plotted against the number of echoes for both classic IDEAL and $T2^*$-IDEAL methods. The corresponding echo train duration ranges from 9.2 ms (3 echoes) to 38 ms (12 echoes). As can be seen, the fat-signal fraction values calculated from classic IDEAL appear inconsistent due to confounding effect from the $T2^*$ decay. In contrast, $T2^*$-IDEAL provides stable estimation, so long as 4 or more are used. This study demonstrates the importance of $T2^*$ correction when quantifying hepatic steatosis, even in the presence of a normal $T2^*$ decay. Imaging parameters include: $TE_1=2.8$ ms, $\Delta TE=3.2$ ms, 224×128 matrix, 36×25 cm FOV, BW=±100 kHz. 8 locations were covered in a 29-second breath-hold with no parallel imaging acceleration.

Discussion:

This embodiment of the invention provides a novel multi-echo reconstruction method capable of decoupling and estimating the fat quantity and the $T2^*$ decay. This method shows great potential for simultaneous assessment of fatty infiltration and iron overload in patients with chronic liver disease. The ability to quantify fat and iron simultaneously is of great importance as steatosis and iron overload commonly co-exist in patients with chronic liver disease. To remove these confounding effects, conventional methods require careful design of the imaging parameters (e.g. acquire in-phase images only for $R2^*$ mapping), often leading to limitations in sequence flexibility or multiple breath-holds. Liver biopsy is considered as a gold standard for the measurement of fatty infiltration and iron deposition; however, it is expensive, risky and highly invasive. Both steatosis and iron deposition can also have a heterogeneous distribution, and liver biopsy can only sample limited locations. Therefore, the utility of biopsy for diagnosis and monitoring of liver patients is limited. Similarly, MRS (MR Spectroscopy) can provide accurate measurements, however, it is associated with long scan times and limited sampling locations. Volumetric imaging techniques, such as MRI, enable faster mapping of the fat and iron contents in the entire liver. In-Phase (IP) and Out-of-Phase (OP) imaging has been routinely used and proven to offer high sensitivity and specificity for detecting fatty infiltration. However, to accurately quantify fat, a $T2^*$ map has to be acquired in a separate scan for removing possible confounding effects from $T2^*$ decay. Using IP and OP imaging to detect iron deposition remains limited as it only provides qualitative and indirect information. The $T2^*$-IDEAL technique provided by this embodiment of the invention accounts for the effects of both fat and shortened $T2^*$ and allows flexible and fast acquisitions, therefore, is promising for reliable and rapid measurement of both fat content and the presence of iron.

The multi-echo sequence shown in FIG. 4 allows the collection of more than 3 echoes with a relatively small scan time penalty, improving the noise performance of $R2^*$ estimation. Depending on the specific imaging parameters, it may still be difficult to cover the entire liver in a single breath-hold, and additional acceleration with parallel imaging may be needed particularly for high resolution imaging, as shown in FIG.'s 9A-E. Some of our patient scans shown may have insufficient coverage due to long scan time, which can be resolved by using parallel imaging acceleration in one or more directions. Flyback gradients were used to acquire all echoes in the same readout direction, ensuring that chemical shift artifact was the same for all echoes. Alternating polarity readout gradients would results in misaligned fat (acetone) signals for the echoes acquired with alternating polarity.

The Cramer-Rao Bound construct was used to study the noise performance of the $T2^*$-IDEAL technique and to guide the design of the acquisition strategy. With a fixed first echo and echo spacing, it was found that the ability of a reconstruction method to estimate the $R2^*$, reflected as noise standard deviation of the $R2^*$ map, improves rapidly with the echo train duration (thus number of echoes), and reaches a plateau when the echo train duration is about 3-4 times the actual $T2^*$ value. However, such long echo train duration may not be achievable in practice due to breath-hold constraints. Furthermore, with a fixed TR, acquiring as many echoes as possible always helps to increase the SNR of the decomposed images. Therefore, to achieve the best sequence efficiency, six echoes with minimum echo times were used, along with the shortest possible first echo time. It is important to avoid echo spacings that lead to a water-fat phase shift of $2\pi$, i.e.: in-phase, where decomposition of water from fat becomes ill-conditioned.

The noise performance results shown in FIG.'s 2A-C suggest that it is not possible to achieve $NSA_{eff}$ of 6 for the water and fat images reconstructed from the $T2^*$-IDEAL method. It is perceivable that $T2^*$-IDEAL results in increased noise variance compared with classic IDEAL, because the signal model includes an additional degree of freedom. This noise magnification also comes from the $T2^*$ correction, which leads to different and magnified noise variance in the source images, since there is less signal in the source images with longer echo times. Therefore, the acquisition of additional echoes may in fact result in noisier estimates of water, fat and $R2^*$, if the source images are weighted equally. For this reason, we chose a weighted least square inversion approach that automatically takes into account this difference and has been shown to achieve the Cramer-Rao Bound, the best possible noise performance. Consequently the acquisition of more echoes improves the SNR of the decomposed images, although with diminishing returns. As suggested in FIG.'s 2A-C, it is important to use a minimum possible first echo $TE_1$, to maximize noise performance because the signal at $TE_1$, has the highest SNR among all source signals. Although we only showed CRB for equally spaced echo times, studies with arbitrary echo times showed similar behavior and no significant improvement of the noise performance has been found with non-equally spaced echoes.

Despite the Cramer-Rao Bound, there are ways to improve noise performance by taking advantage of a priori information or using regularization methods. For example, by constraining the possible value of R2* to greater than 0 and less than a pre-defined upper bound, erroneous or non-physical R2* values can be avoided. This is most useful when long T2*, and thus small R2* values, are expected. Additionally, it is frequently assumed that the field map and the R2* map are spatially slowly varying. Thus applying a spatially smoothing filter to the field map and the R2* map may improve the noise performance while still maintaining relatively good accuracy in the estimates of R2*. Finally, it is important to note that the same data can be reconstructed with the classic IDEAL algorithm, obtaining higher SNR water and fat images, but with the risk of bias from the confounding effects of shortened T2*.

A major assumption of the T2*-IDEAL technique is that water and fat that co-exist in a voxel, will have the same T2* relaxation. With severe iron overload T2* decay is dominated by the presence of iron and this may be a reasonable assumption. With mild or no iron present, the T2* values of the water and fat within a voxel may be different. However, a previous study has shown that fat-signal fraction calculated from a single-valued T2* correction is within 10% of the true percentage when the T2* value is 35 ms for fat and 25 ms for water. The algorithm may be extended to estimate multi-component T2* decays.

The application of this invention is not limited in liver imaging. Accurate fat or T2* quantification can also be useful in other applications such as determining the blood oxygen level, diagnosis of bone marrow diseases, quantitative characterization of adrenal masses and quantification of iron deposition in heart.

The accuracy of the T2*-IDEAL technique, including the T2* estimation and fat quantification, requires clinical validation. Ultimately, co-registration of biopsy with the results from T2*-IDEAL reconstruction must be performed in order to obtain a meaningful correlation.

Therefore, this embodiment provides an algorithm that can achieve chemical species separation and T2* quantification simultaneously. As a result, the scope of applications for water-fat decomposition methods is greatly extended. This embodiment provides technique for quantitative assessment of patients with chronic liver diseases with concomitant hepatic steatosis and iron overload.

An Example of a Modified IDEAL Algorithm To Calculate the Complex Field Map $\hat{\psi}$ With the signals collected at all echoes, Eq. [1] can be formatted in a matrix form:

$$s = \begin{bmatrix} s_1 \\ s_2 \\ \dots \\ s_k \end{bmatrix} = \begin{bmatrix} e^{j2\pi\hat{\psi}t_1} & 0 & \dots & 0 \\ 0 & e^{j2\pi\hat{\psi}t_2} & \dots & 0 \\ \dots & \dots & \dots & \dots \\ 0 & 0 & \dots & e^{j2\pi\hat{\psi}t_k} \end{bmatrix} \cdot \begin{bmatrix} 1 & e^{j2\pi\Delta f t_1} \\ 1 & e^{j2\pi\Delta f t_2} \\ \dots & \\ 1 & e^{j2\pi\Delta f t_k} \end{bmatrix} \cdot \begin{bmatrix} w \\ f \end{bmatrix} \quad [A.1]$$

$$= P(\hat{\psi}) \cdot A \cdot p$$

where $$P(\hat{\psi}) = \begin{bmatrix} e^{j2\pi\hat{\psi}t_1} & 0 & \dots & 0 \\ 0 & e^{j2\pi\hat{\psi}t_2} & \dots & 0 \\ \dots & \dots & \dots & \dots \\ 0 & 0 & \dots & e^{j2\pi\hat{\psi}t_k} \end{bmatrix}_{k \times k}$$

$$A = \begin{bmatrix} 1 & e^{j2\pi\Delta f t_1} \\ 1 & e^{j2\pi\Delta f t_2} \\ \dots & \\ 1 & e^{j2\pi\Delta f t_k} \end{bmatrix}_{k \times 2}, \rho = \begin{bmatrix} w \\ f \end{bmatrix}_{2 \times 1}$$

The vector s denotes the acquired signals. The matrix A is considered known. The matrix $P(\hat{\psi})$ is a function of the complex field map and represents the field map and R2* modulation on the signals. The noise term in Eq. [1] has been dropped for convenience. The following algorithm is used to estimate the complex field map $\hat{\psi}$ on a pixel-by-pixel basis:

1. Starting from the initial guess of the complex field map $\tilde{\psi} = \psi_0$. In one example, $\psi_0$ is determined by the region growing process, described in Yu H, Reeder SB, Shimakawa A, Brittain JH, and Pelc NJ. Field map estimation with a region growing scheme for iterative 3-point water-fat decomposition. Magn Reson Med 2005;54(4):1032-1039, to address the field map ambiguity problem. An initial guess of 0 is used for R2* at all pixels as no similar ambiguity problem is found for R2*. $\tilde{\psi}$ represents the current estimate of the "complex field map".

2. With the estimated $\tilde{\psi}$, the corresponding complex water $\tilde{w}$ and fat $\tilde{f}$ can be determined from a least squares inversion:

$$\tilde{\rho} = \begin{bmatrix} \tilde{w} \\ \tilde{f} \end{bmatrix} = (A^T A)^{-1} A^T \cdot P(-\tilde{\psi}) \cdot s \quad [A.2]$$

where $A^T$ represents the complex conjugate transpose of the A matrix. Here, the fact that $P(-\tilde{\psi}) \cdot P(\tilde{\psi}) = P(\tilde{\psi}) \cdot P(-\tilde{\psi}) = I$ is used.

3. Eq. [1] can be approximated by Taylor expansion as in the following, with the $2^{nd}$ and higher order terms neglected.

$$s_i = (\tilde{w} + \tilde{f} \cdot e^{j2\pi\Delta f t_i}) \cdot e^{j2\pi\tilde{\psi} t_i} + e^{j2\pi\tilde{\psi} t_i} \cdot \Delta w +$$
$$e^{j2\pi\tilde{\psi} t_i} \cdot e^{j2\pi\Delta f t_i} \Delta f + (\tilde{w} + \tilde{f} \cdot e^{j2\pi\Delta f t_i}) \cdot e^{j2\pi\tilde{\psi} t_i} \cdot j2\pi t_i \cdot \Delta \hat{\psi} \quad [A.3]$$

Considering all echoes, Eq. [A.3] can be formulated in a matrix form:

$$s = P(\tilde{\hat{\psi}}) \cdot A \cdot \tilde{p} + P(\tilde{\hat{\psi}}) \cdot \begin{bmatrix} (\tilde{w}+\tilde{f}\cdot e^{j2\pi\Delta f t_1})\cdot j2\pi t_1 & 1 & e^{j2\pi\Delta f t_1} \\ (\tilde{w}+\tilde{f}\cdot e^{j2\pi\Delta f t_2})\cdot j2\pi t_2 & 1 & e^{j2\pi\Delta f t_2} \\ \cdots & \cdots & \cdots \\ (\tilde{w}+\tilde{f}\cdot e^{j2\pi\Delta f t_k})\cdot j2\pi t_k & 1 & e^{j2\pi\Delta f t_k} \end{bmatrix} \cdot \begin{bmatrix} \Delta\hat{\psi} \\ \Delta w \\ \Delta f \end{bmatrix}$$

$$= P(\tilde{\hat{\psi}}) \cdot A \cdot \tilde{p} + P(\tilde{\hat{\psi}}) \cdot B(\tilde{w},\tilde{f}) \cdot \begin{bmatrix} \Delta\hat{\psi} \\ \Delta w \\ \Delta f \end{bmatrix}$$

[A.4]

where, $$B(\tilde{w},\tilde{f}) = \begin{bmatrix} (\tilde{w}+\tilde{f}\cdot e^{j2\pi\Delta f t_1})\cdot j2\pi t_1 & 1 & e^{j2\pi\Delta f t_1} \\ (\tilde{w}+\tilde{f}\cdot e^{j2\pi\Delta f t_2})\cdot j2\pi t_2 & 1 & e^{j2\pi\Delta f t_2} \\ \cdots & \cdots & \cdots \\ (\tilde{w}+\tilde{f}\cdot e^{j2\pi\Delta f t_k})\cdot j2\pi t_k & 1 & e^{j2\pi\Delta f t_k} \end{bmatrix}_{k\times 3}$$

Therefore, error terms can be obtained by another least squares inversion:

$$\begin{bmatrix} \Delta\hat{\psi} \\ \Delta w \\ \Delta f \end{bmatrix} = (B^T B)^{-1} B^T \cdot \left( P(-\tilde{\hat{\psi}}) \cdot s - A \cdot \tilde{p} \right) \quad [A.5]$$

where $B(\tilde{w}, \tilde{f})$ has been simplified as B.

4. Update the estimated complex field map:

$$\tilde{\hat{\psi}} = \tilde{\hat{\psi}} + \Delta\hat{\psi} \quad [A.6]$$

5. With the new $\tilde{\hat{\psi}}$, repeat step 2-4 until the following convergence criterion is achieved or a pre-defined maximum number of iterations (30) is met:

$$|\text{real}\{\Delta\hat{\psi}\}| = |\text{real}\{\Delta\psi\}| < \epsilon \text{ and }$$

$$|\{\Delta\hat{\psi}\}\cdot 2\pi| = |\text{imag}\{R^*_2\}| < \epsilon \quad [A.7]$$

where $\epsilon$ denotes a small number. In practice, $\epsilon=1$ can be used.

Compared to the classic IDEAL iteration, the described algorithm estimates two parameters ($\psi$ and R2*) during the iteration. Despite the complications added by the 2-dimensional search, this iteration algorithm behaves well and typically converges within 10 iterations. For acquisitions with severe iron overload, the SNR of the source signals in liver may be limited. In these cases, a better approach is to first perform a classic IDEAL iteration to estimate the field map using the first three echoes. The resultant field map then is used as an initial guess for T2*-IDEAL iteration, leading to a faster iterations completed typically in 2-3 iterations. The "pre-conditioning" step (3-pt classic IDEAL iteration) normally involves less than 5 iterations. Therefore, both performance and convergence behavior are improved. Finally, the calculation of Eq. [A.5] can be further optimized to achieve faster iterations.

OTHER EMBODIMENTS

More generally, the invention provides an estimated decay map that is used to generate an image for at least two different species. FIG. 11 is a high level flow chart of an embodiment of the invention. A magnetic image excitation is applied for a plurality of cycles (step 1104). A plurality of magnetic resonance image echoes is acquired for each cycle (step 1108). A decay map is estimated (step 1112). An image is generated (step 1116).

FIG. 12 is a schematic top view of a magnetic resonance imaging (MRI) system 1200 that may be used in an embodiment of the invention. The MRI system 1200 comprises a magnet system 1204, a patient transport table 1208 connected to the magnet system, and a controller 1212 controllably connected to the magnet system. In one example, a patient would lie on the patient transport table 1208 and the magnet system 1204 would pass around the patient. The controller 1212 would control magnetic fields and radio frequency (RF) signals provided by the magnet system 1204 and would receive signals from detectors in the magnet system 1204.

Figure 13A:
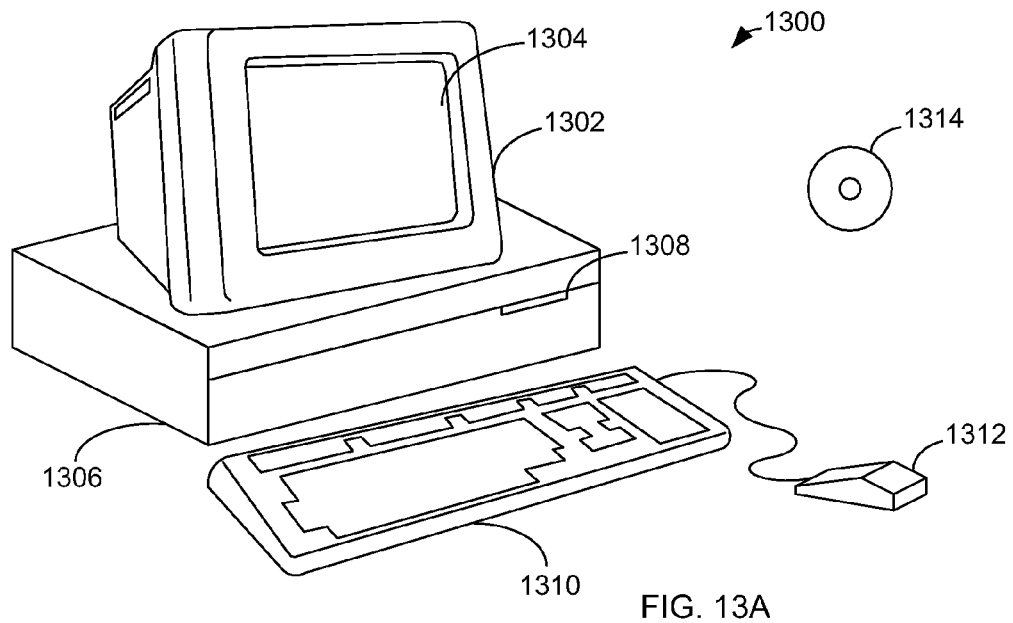

FIG.'s 13A and 13B illustrate a computer system 1300, which is suitable for implementing a controller 1212 used in embodiments of the present invention. FIG. 13A shows one possible physical form of the computer system. Of course, the computer system may have many physical forms ranging from an integrated circuit, a printed circuit board, and a small handheld device up to a huge super computer. Computer system 1300 includes a monitor 1302, a display 1304, a housing 1306, a disk drive 1308, a keyboard 1310, and a mouse 1312. Disk 1314 is a computer-readable medium used to transfer data to and from computer system 1300.

Figure 13B:
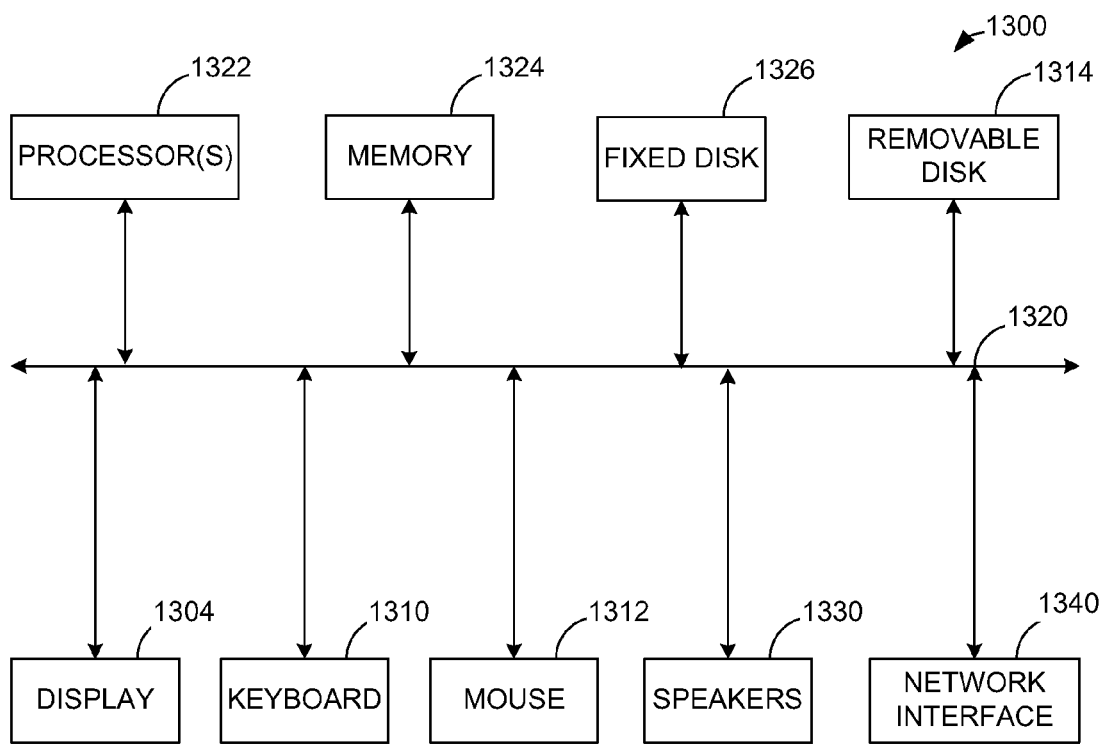

FIG. 13B is an example of a block diagram for computer system 1300. Attached to system bus 1320 are a wide variety of subsystems. Processor(s) 1322 (also referred to as central processing units, or CPUs) are coupled to storage devices, including memory 1324. Memory 1324 includes random access memory (RAM) and read-only memory (ROM). As is well known in the art, ROM acts to transfer data and instructions uni-directionally to the CPU and RAM is used typically to transfer data and instructions in a bi-directional manner. Both of these types of memories may include any suitable of the computer-readable media described below. A fixed disk 1326 is also coupled bi-directionally to CPU 1322; it provides additional data storage capacity and may also include any of the computer-readable media described below. Fixed disk 1326 may be used to store programs, data, and the like and is typically a secondary storage medium (such as a hard disk) that is slower than primary storage. It will be appreciated that the information retained within fixed disk 1326 may, in appropriate cases, be incorporated in standard fashion as virtual memory in memory 1324. Removable disk 1314 may take the form of the computer-readable media described below.

CPU 1322 is also coupled to a variety of input/output devices, such as display 1304, keyboard 1310, mouse 1312, and speakers 1330. In general, an input/output device may be any of: video displays, track balls, mice, keyboards, microphones, touch-sensitive displays, transducer card readers, magnetic or paper tape readers, tablets, styluses, voice or handwriting recognizers, biometrics readers, or other computers. CPU 1322 optionally may be coupled to another computer or telecommunications network using network interface 1340. With such a network interface, it is contemplated that the CPU might receive information from the network, or might output information to the network in the course of performing the above-described method steps. Furthermore, method embodiments of the present invention may execute solely upon CPU 1322 or may execute over a network such as the Internet in conjunction with a remote CPU that shares a portion of the processing.

In addition, embodiments of the present invention further relate to computer storage products with a computer-readable medium that has computer code thereon for performing various computer-implemented operations. The media and computer code may be those specially designed and constructed for the purposes of the present invention, or they may be of the kind well known and available to those having skill in the computer software arts. Examples of computer-readable media include, but are not limited to: magnetic media such as hard disks, floppy disks, and magnetic tape; optical media such as CD-ROMs and holographic devices; magneto-optical media such as floptical disks; and hardware devices that are specially configured to store and execute program code, such as application-specific integrated circuits (ASICs), programmable logic devices (PLDs) and ROM and RAM devices. Examples of computer code include machine code, such as produced by a compiler, and files containing higher level code that are executed by a computer using an interpreter. Computer readable media may also be computer code transmitted by a computer data signal embodied in a carrier wave and representing a sequence of instructions that are executable by a processor.

Various examples that use the inventive method and apparatus will be provided.

An example of a first species may be fat. The first species signal may be conditioned. The conditioning may provide chemical shift, rescale intensity, weighting, shifted in space, rotated, or another re-orientation, or another mathematical operation may be performed on the first species signal. Other examples may not provide this conditioning step.

An example of a second species may be water, so that the first species and second species are different. The second species signal may be conditioned. The conditioning may provide chemical shift, rescale intensity, shifted in space, rotated, or another re-orientation or spatial shift, or another mathematical operation may be performed on the second species signal. Other embodiments may not provide this conditioning step.

An example of the invention estimates relaxation times ($T_1$, $T_2$, $T_2^*$) and corrects the relaxation times for quantification of a species. Species that have a short $T_1$ recover faster and therefore have a higher intensity signal, appearing brighter than other species. A correction factor (or weight) may be used to correct this. The measured $T_2^*$ can be used to correct for short $T_2^*$ decay. Different species such as fat and water may require different corrections. By providing a separate fat signal and a separate water signal, the different corrections may be provided to the different signals.

In the specification and claims the estimating a decay map and using the estimated decay map to generate an image may be done on a pixel-by-pixel basis or may be an image based process.

U.S. patent application Ser.No. 11/738,339 by Scott B. Reeder et al., entitled "MRI METHODS FOR COMBINING SEPARATE SPECIES AND QUANTIFYING A SPECIES" filed concurrently herewith, teaches MRI methods for combining separate species and quantifying a species; U.S. patent application Ser. No. 11/738,340 by Charles A. McKenzie et al., entitled "SELF-CALIBRATION METHODS FOR PARALLEL IMAGING AND MULTIPOINT WATER-FAT SEPARATION METHODS" filed concurrently herewith, teaches self-calibration methods for parallel imaging and multipoint water-fat separation methods; U.S. patent application Ser. No. 11/738,343 by Angel R. Pineda et al., entitled "MAXIMUM LIKELIHOOD ESTIMATOR IN THE PRESENCE OF NON-IDENTICALLY DISTRIBUTED NOISE FOR DECOMPOSITION OF CHEMICAL SPECIES IN MRI" filed concurrently herewith, teaches maximum likelihood estimator in the presence of non-identically distributed noise for decomposition of chemical species in MRI; U.S. patent application Ser. No. 11/738,345 by Zhifei Wen et al., entitled "REGULARIZED SPECIES SEPARATION" filed concurrently herewith, teaches regularized species separation; U.S. patent application Ser. No. 11/738,347by Huanzhou Yu et al., entitled "SLIDING WINDOW RECONSTRUCTION AND PHASE/FIELD MAP UPDATING FOR DYNAMIC CHEMICAL SHIFT IMAGING" filed concurrently herewith, teaches sliding window reconstruction and phase/field map updating for dynamic chemical shift imaging; U.S. patent application Ser. No. 11/738,352 by Charles A. McKenzie et al., entitled "CALIBRATION MAPS FOR PARALLEL IMAGING FREE OF CHEMICAL SHIFT ARTIFACT" filed concurrently herewith, teaches calibration maps for parallel imaging free of chemical shift artifact, all of which are incorporated by reference herein.

While this invention has been described in terms of several preferred embodiments, there are alterations, permutations, modifications and various substitute equivalents, which fall within the scope of this invention. It should also be noted that there are many alternative ways of implementing the methods and apparatuses of the present invention. It is therefore intended that the following appended claims be interpreted as including all such alterations, permutations, modifications, and various substitute equivalents as fall within the true spirit and scope of the present invention.

What is claimed is:

1. A method for generating a magnetic resonance image, comprising:
   a) applying a magnetic resonance imaging excitation for a plurality of cycles at a cycle rate;
   b) acquiring a plurality of magnetic resonance image echoes for each cycle;

c) estimating a decay map from the plurality of magnetic resonance image echoes for each cycle; and d) using the estimated decay map to generate an image for at least two different species.

2. The method, as recited in claim 1, wherein there exists at least two of the plurality of magnetic resonance image echoes for each cycle that their species phase angle difference is not $k*\pi$, where k is an integer.

3. The method as recited in claim 2, wherein the using the estimated decay map to generate an image for at least two different species applies a least squares process with the estimated decay map to determine species intensity.

4. The method as recited in claim 3, wherein the applied least squares process is an applied weighted least squares process.

5. The method, as recited in claim 4, wherein the weighted least squares process provides a lower weight to more decayed signals.

6. The method, as recited in claim 5, wherein the at least two different species are water and fat.

7. The method, as recited in claim 6, further comprising using the estimated decay map to generate an oxygen level map.

8. The method, as recited in claim 7, further comprising using the estimated decay map to generate an iron level map.

9. The method, as recited in claim 8, wherein the iron level map is used to generate the image for at least two species.

10. The method of claim 9, wherein the estimating a decay map from the plurality of magnetic resonance image echoes for each cycle uses at least two echoes per cycle.

11. The method of claim 9, wherein the estimating a decay map from the plurality of magnetic resonance image echoes for each cycle uses at least three echoes per cycle.

12. The method of claim 9, wherein the estimating a decay map from the plurality of magnetic resonance image echoes for each cycle uses at least six echoes per cycle.

13. The method, as recited in claim 1, wherein the at least two different species are water and fat.

14. The method, as recited in claim 1, further comprising using the estimated decay map to generate an oxygen level map.

15. The method, as recited in claim 1, further comprising using the estimated decay map to generate an iron level map.

16. The method, as recited in claim 1, further comprising estimating a field map from the plurality of magnetic resonance image echoes for each cycle.

17. The method of claim 1, wherein the estimating a decay map from the plurality of magnetic resonance image echoes for each cycle uses at least six echoes per cycle.

18. An apparatus for providing magnetic resonance images, comprising:

a magnet system;

a controller electrically connected to the magnet system, comprising:

a display;

at least one processor; and computer readable media, comprising:

computer readable code for applying a cyclical magnetic resonance imaging excitation for a plurality of cycles at a cycle rate;

computer readable code for acquiring a plurality of magnetic resonance image echoes for each cycle;

computer readable code for estimating a decay map from the plurality of magnetic resonance image echoes for each cycle;

computer readable code for using the estimated decay map to generate an image for at least two different species; and computer readable code for displaying the generated image on the display.

19. The apparatus as recited in claim 18, wherein the using the estimated decay map to generate an image for at least two different species applies a least squares process with estimated decay to determine species intensity.

20. The apparatus as recited in claim 18, wherein the computer readable media further comprises computer readable code for estimating a decay map from the plurality of magnetic resonance image echoes for each cycle.

* * * * *